United States Patent [19]

Molino

[11] Patent Number: 5,779,735
[45] Date of Patent: Jul. 14, 1998

[54] KNEE UNIT FOR ABOVE-KNEE PROSTHETIC LEG

[76] Inventor: Joseph L. Molino, 2 Aura Dr., Valley Cottage, N.Y. 10989

[21] Appl. No.: 650,898

[22] Filed: May 17, 1996

Related U.S. Application Data

[63] Continuation of Ser. No. 316,854, Oct. 3, 1994, abandoned.

[51] Int. Cl.$^6$ .................................................. A61F 2/64
[52] U.S. Cl. ............................................. 623/44; 623/43
[58] Field of Search .............................. 623/44, 43, 26, 623/45, 24, 25, 39–42, 46; 267/113, 118, 124

[56] References Cited

U.S. PATENT DOCUMENTS

| | | | |
|---|---|---|---|
| 2,605,474 | 8/1952 | Oliver | 623/44 X |
| 3,648,294 | 3/1972 | Shahrestani | 623/22 |
| 3,799,159 | 3/1974 | Scott | 623/39 X |
| 4,311,302 | 1/1982 | Heyer et al. | 267/64.23 |
| 4,958,705 | 9/1990 | Horvath | 188/314 |
| 5,062,856 | 11/1991 | Sawamura et al. | 623/24 |
| 5,062,857 | 11/1991 | Berringer et al. | 623/25 |
| 5,092,902 | 3/1992 | Adams et al. | 623/26 |
| 5,376,137 | 12/1994 | Shorter et al. | 623/44 |
| 5,376,138 | 12/1994 | Bouchard | 623/44 |

FOREIGN PATENT DOCUMENTS

| | | | |
|---|---|---|---|
| 565074 | 10/1958 | Canada | 188/315 |
| 2146840 | 3/1973 | Germany | 188/315 |
| 9222267 | 12/1992 | WIPO | 623/44 |

*Primary Examiner*—David H. Willse
*Attorney, Agent, or Firm*—Lawrence G. Fridman; Anthony F. Cuoco

[57] ABSTRACT

A knee unit for an above-knee prosthetic leg includes a piston arrangement, a valve arrangement and a bladder arrangement for achieving swing and stance control of the prosthetic leg. For swing control the piston arrangement displaces a fluid through the valve arrangement to compress the bladder arrangement for storing the energy required to drive an extension cycle of the prosthetic leg and to provide bias and flexion resistance for the knee unit. For stance control the valve arrangement is such that when weight is applied to the heel of a prosthetic foot at various stages of the gait cycle of the prosthetic leg, the knee unit is permitted to flex or is prevented from flexing via compression of the bladder to provide stability during the various phases of the gait cycle.

16 Claims, 5 Drawing Sheets

KNEE UNIT FOR ABOVE-KNEE PROSTHETIC LEG

This is a continuation of application Ser. No. 08/316,854 filed on Oct. 3, 1994, now abandoned.

BACKGROUND OF THE INVENTION

This invention relates to a fluid controlled knee unit for an above-knee prosthetic leg and, more particularly, to a knee unit of the type described which in one form of the invention is operable for swing control and in another form of the invention is operable for stance control.

In an above-knee prosthetic leg, the swing of the knee and shank of the leg is controlled in an effort to duplicate the function of a normal knee produced by the quadriceps and hamstring muscle group during the swing phase of gait. Stance control is used to lock the prosthetic leg to prevent buckling when the heel strikes a walking surface and to unlock the leg when the weight of an amputee is transferred from heel to toe.

One of the primary problems in providing a satisfactory above-knee prosthetic leg involves swing control so that movement by the amputee at varying speeds can be comfortably accomplished. This can be achieved by fluid or friction controlled systems. Fluid controlled systems are advantageous in this regard since with friction systems the operation of the system is constant with respect to speed and therefore the amputee must make adjustments to the prosthetic leg to vary the speed of movement, as may be required.

Fluid controlled systems, on the other hand, can suffer from viscosity, or resistance to fluid flow, and are greatly affected by temperature changes and suffer from fluid leakage. The proper choice of a fluid and seal arrangement, as accomplished by the present invention, minimizes these problems and others usually associated with fluid controlled systems.

SUMMARY OF THE INVENTION

This invention contemplates a fluid controlled knee unit for an above-knee prosthetic leg including a piston arrangement, a valve arrangement and a bladder arrangement. In one form of the invention, swing control of the prosthetic leg is achieved and in another form of the invention, stance control is achieved.

For swing control, use of the prosthetic leg displaces the piston arrangement, whereupon a fluid passes through the valve arrangement which includes an adjustable flow control valve and a check valve to the bladder arrangement. The piston arrangement provides a complete fluid seal with a minimum of friction and is self-adjusting for a maximum seal during displacement.

The bladder arrangement is affected by the fluid for storing all energy necessary to drive an extension cycle of the prosthetic leg and also provides bias and flexion resistance for the knee unit. The rate of extension of the prosthetic leg is controlled by adjustment of check valve pressure and pressure within the bladder arrangement. To this extent, the bladder arrangement has a valve which is used to provide an adjustable bladder resistance, flexion resistance and extension cycle. The bladder arrangement also eliminates the need for a complex arrangement to accommodate fluid displaced during the flexion cycle.

During extension of the prosthetic leg the pressure adjustment to the bladder arrangement and the check valve provides precise knee unit extension bias control. Additionally, the bladder arrangement provides a pressurized arrangement to preclude the possibility of air entering the piston chamber, as will be recognized as advantageous.

For stance control a stance valve is arranged with the flow control valve and is actuated by a linkage coupled to a lever via a choke type cable or alternatively, by an electrical switch and a servo mechanism. The arrangement is such that when weight is applied to the heel at various stages of the gait cycle of the prosthetic leg, the stance valve is operated via the lever, whereby the knee unit is prevented from flexing or permits flexing, as the case may be. This provides the required stability at heel strike and through the midstance portion of the gait cycle to provide safe and efficient ambulation for the amputee. The arrangement is such that the valve enables flexion of the knee during the heel-off, toe-off and swing phase portions of the gait cycle.

DETAILED DESCRIPTION OF THE INVENTION

Figure 1:
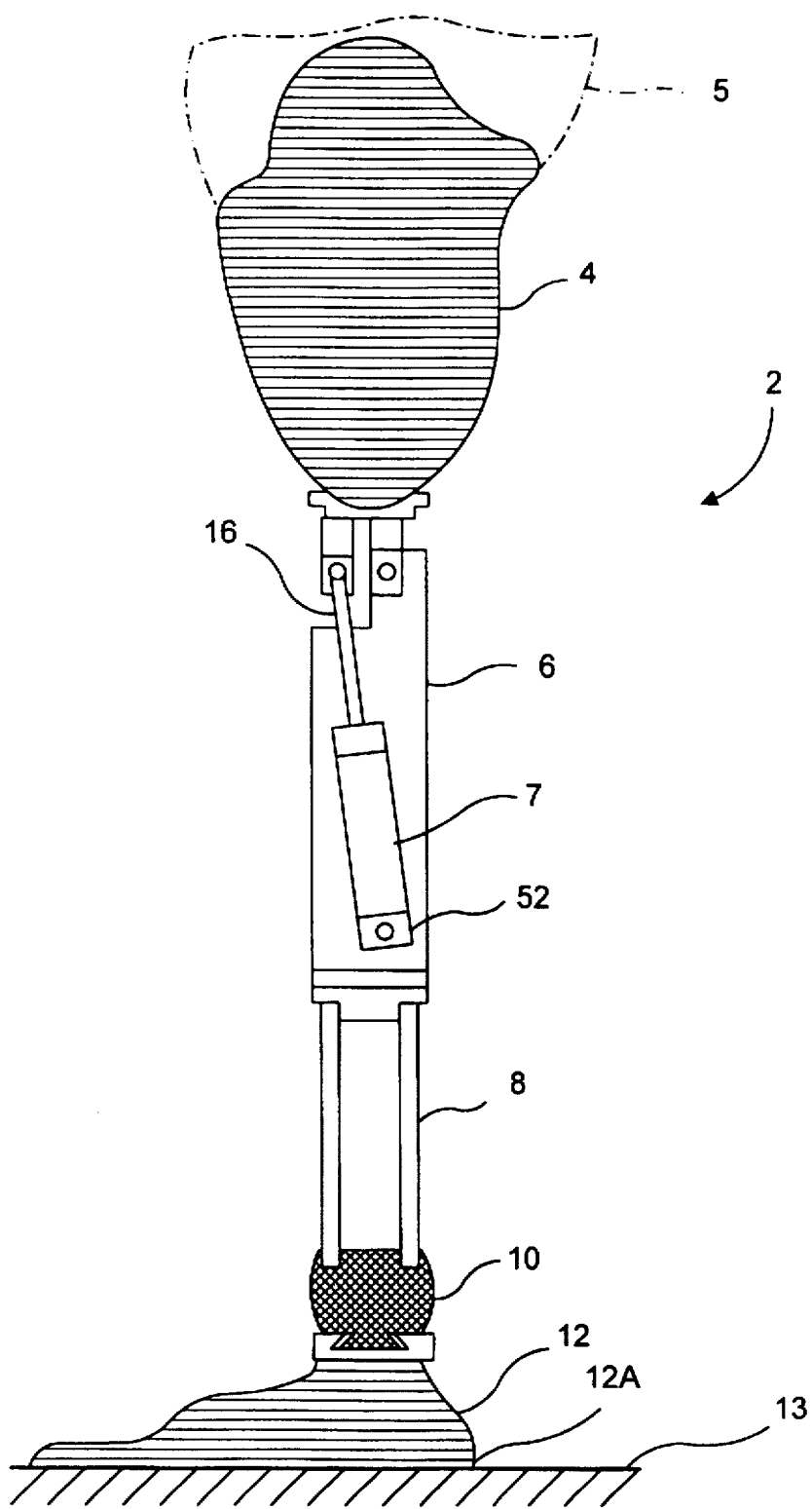
FIG. 1 is a diagrammatic representation generally illustrating an above-knee prosthetic leg incorporating the invention.

With reference first to FIG. 1, an above-knee prosthetic leg is designated generally by the numeral 2. Prosthetic leg 2 includes a socket 4 of a suitable material such as plastic for receiving a leg stump 5 of an amputee, and which socket 4 is coupled by conventional means to the top of a knee cage 6. Knee cage 6 supports a knee control unit 7 which is arranged for swing control or phase control as will be hereinafter described. A pylon 8 is coupled to the bottom of knee cage 6 by conventional means and is coupled by likewise conventional means via a pyramid connector 10 to a prosthetic foot 12.

Figure 2:
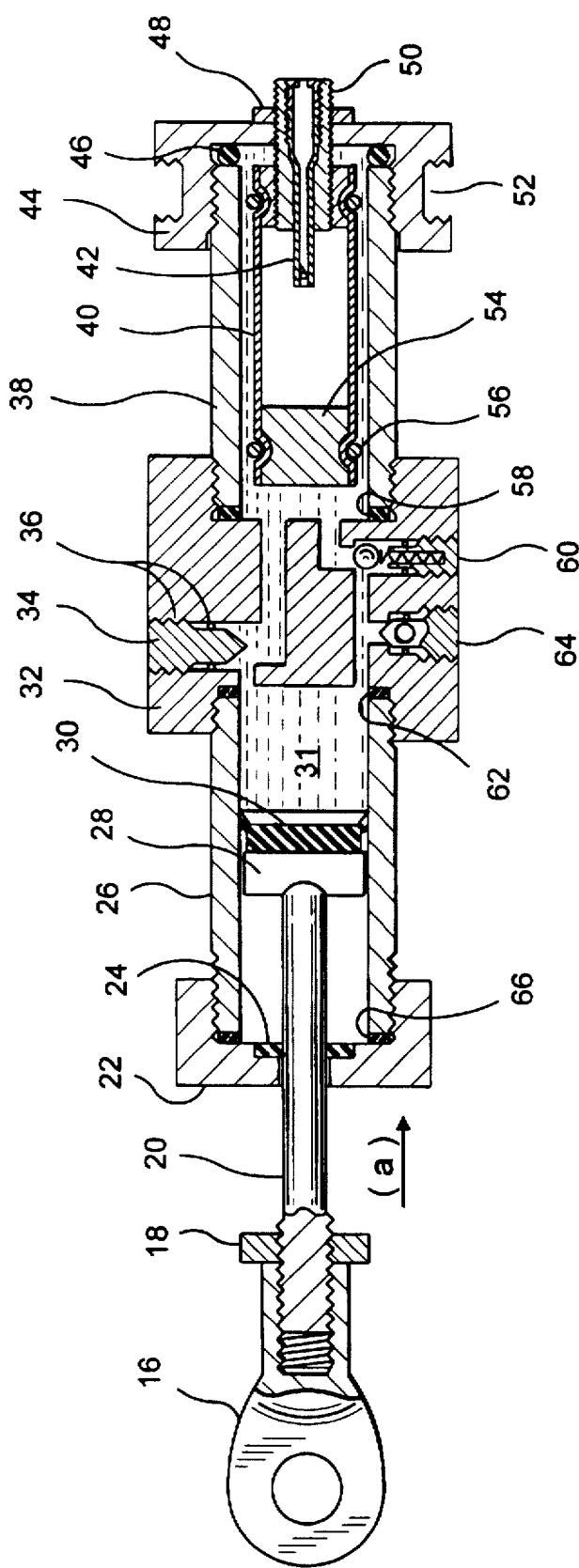
FIG. 2 is a schematic representation particularly illustrating a form of the invention wherein a knee unit is arranged for swing control according to the invention.

FIG. 2 illustrates a knee control unit 7A for swing control in accordance with the invention. Thus, a pivot mount 16 which couples unit 7A to cage 6 (FIG. 1) is coupled via a length adjusting nut 18 to a piston rod 20. Piston rod 20 extends through a piston cap 22 via a bushing 24 and extends into a piston cylinder 26. A plunger block 28 within cylinder 26 is coupled to a piston 30. Piston cylinder 26 contains therein a suitable fluid 31 which may be, for purposes of illustration, a silicone oil. A valve body 32 is coupled to cylinder 26 and supports a flow control valve 34 via a seal 36.

A bladder cylinder is designated by the numeral 38. A bladder 40 is disposed within bladder cylinder 38 and includes a bladder valve 42. A cap 44 and a cap seal 46 are coupled to bladder cylinder 12. A valve nut 48 is in threaded engagement with a valve housing 50.

A mount receiver 52 is coupled to bladder cylinder 38. A bladder plug 54 is arranged with bladder 40 and bladder retaining rings 56 retain bladder 40 within bladder cylinder 38. Mount receiver 52 couples unit 7A to cage 6 (FIG. 1).

A seal 58 is disposed between bladder cylinder 38 and valve body 32. Valve body 32 supports a check valve 60.

A seal 62 is disposed between piston cylinder 26 and valve body 32. Valve body 32 supports a bleeder valve 64. A seal 66 is disposed between piston cap 22 and piston cylinder 26.

With the arrangement described, when piston rod 20 is displaced in the direction of arrow (a) upon an amputee using prosthetic leg 2, fluid 31 passes through flow control valve 34 which is adjustable in valve body 9. Check valve 60 prohibits fluid passage through its port during the flexion of knee control unit 7A and only allows fluid flow through flow control valve 34. In this regard, it is noted that there are no O-ring seals associated with the piston arrangement. It will be recognized by those skilled in the art that these seals are a source of excessive friction, leakage and wear. The arrangement described including piston rod 20 and plunger block 28 provides an even and thorough seal with a minimum of friction and provides self-adjustment for maximum sealing during the flexion phase, as will now be recognized.

Most significantly is the arrangement of bladder 40 and its associated components. Bladder 40 is uniquely affected by the operation of valves 34, 60 and 64 as aforenoted so as to be compressed for storing all of the energy necessary to drive an extension cycle of knee control unit 7A, and also provides necessary knee control unit bias and flexion resistance. The rate of extension during the extension cycle can be controlled by a combination of adjustments to check valve 60, i.e. pressure adjustment, and the pressure within the bladder. Valve 42 is adjustable for varying bladder compression, flexion resistance and extension drive.

Bladder 40 also eliminates the need to incorporate fluid passages and an accumulator chamber to accommodate fluid displaced during the flexion phase. During the extension cycle, bladder 40 and the pressure adjustment achieved via check valve 60 provide precise knee unit extension bias control. In this regard, it is noted that if quick initial knee extension is desired, the check valve adjustment is set to provide minimum spring pressure and to therefore utilize the check valve passage as an additional port to regulate the extension cycle. After check valve 60 closes, fluid flow will continue to pass through flow control valve 34 until the completion of the extension cycle. An additional advantage of the bladder arrangement is that it will always provide a pressurized system so as to eliminate the possibility of air getting into the piston chamber.

Figure 3:
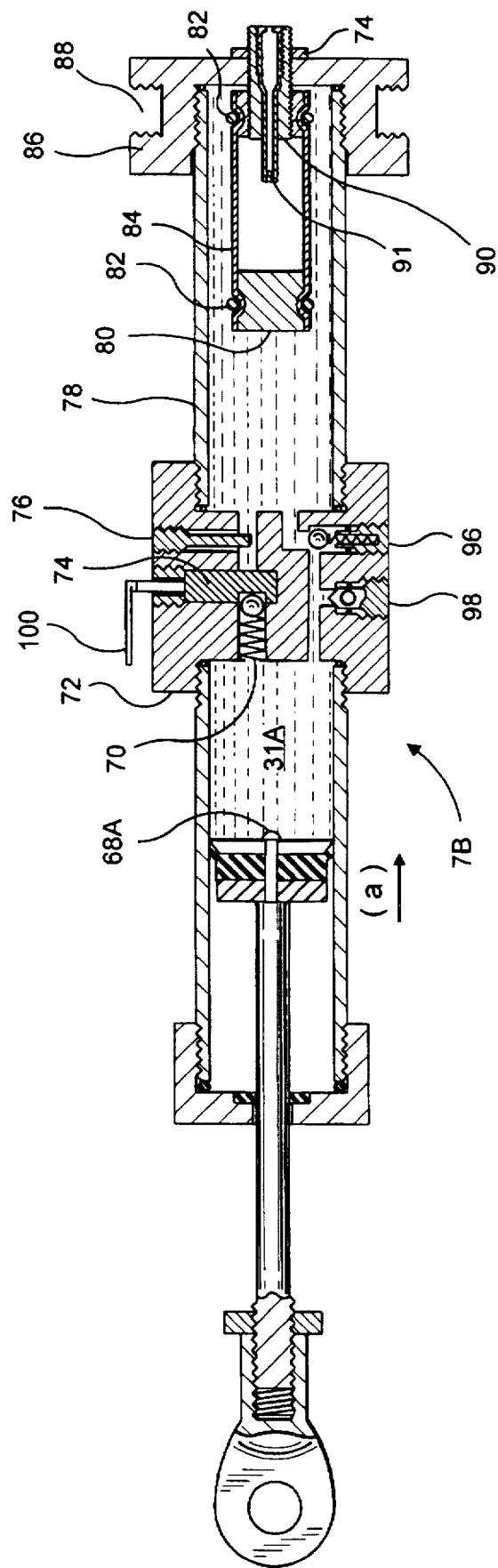
FIG. 3 is a schematic representation particularly illustrating a form of the invention wherein a knee unit is arranged for stance control according to the invention.

FIG. 3 illustrates a knee control unit 7B for stance control in accordance with the invention. Many of the components in unit 7B are similar in construction and function as like components in unit 7A as heretofore described with reference to FIG. 2. Actually, the only difference between the control units described in FIGS. 2 and 3 is the valve arrangement, and which difference will be next described.

Thus, and with particular reference to FIG. 3, when prosthetic leg 2 (FIG. 1) is advanced in the gait cycle, piston plunger 68A forces fluid 31A against a check valve 70 supported in a valve body 72. Valve 70 is disposed ahead of a flow control valve 76 and is normally open, fluid is allowed to flow past the check valve around a valve cam 74 through flow control valve 76 for affecting bladder 84 by compressing the bladder. Energy is thereby stored in the bladder, and which energy extends flexed prosthetic leg 2 thereby making the leg ready for the next part of the gait cycle. With further regard to valve body 72, the valve body supports check valve 96 and bleeder valve 98, for the purposes heretofore described with reference to valves 60 and 64 shown in FIG. 2.

The gait cycle of prosthetic leg 2 has five stages: the heel strike stage; the flat foot stage; the mid-stance stage; the heel off stage; and the toe off stage.

At heel strike, heel 12A of prosthetic foot 12 (FIG. 1) makes initial contact with a walking surface 13 (FIG. 1). At this time, substantial stability is necessary to prevent knee unit 7B from flexing. In an individual having both legs, the action of the quadriceps muscles keeps the knee from flexing at this stage of the gait cycle. With an amputee, as is herein considered, this must be accomplished in a mechanical manner, since the quadriceps muscles and the knee are not present.

The stability of knee control unit 7B is established by closing check valve 70. When heel 12A strikes surface 13 and weight is transferred to the heel, the arrangement of prosthetic foot 12 is such that heel 12A compresses at the time of heel strike. This action moves the weight line forward to help stabilize knee control unit 7B. This heel compression is used to move a valve lever 100 which is mechanically or electrically operated, as will hereinafter be further described. This, in turn, displaces stance valve cam 74 which allows valve 70 to seat and to thereby prevent the flow of fluid 31A to lock-up of knee control unit 7B, whereby flexing of the knee unit is inhibited and the necessary stability is provided.

The flat foot stage of the gait cycle begins immediately after heel 12A strikes walking surface 13, to a point when prosthetic foot 12 is flat on said surface. It is important that knee control unit 7B does not flex at this point. If the knee unit does indeed flex, the amputee is unable to transfer weight to prosthetic leg 2 for support. At this point, valve 70 is seated and knee unit 7B is locked.

The mid-stance phase occurs at the point in the gait cycle when prosthetic leg 2 is perpendicular to prosthetic foot 12 and walking surface 13. At this point, prosthetic leg 2 is bearing the weight of the amputee's body. The body weight is transferred through residual stump 5 received in socket 4 (FIG. 1) through knee unit 7B and through the prosthetic lower leg portion, and into and through prosthetic foot 12 to walking surface 13. Knee unit 7B must be locked at this phase of the gait cycle which is accomplished by the closure of valve 70.

At the heel-off phase of the gait cycle, the weight is transferred to the sound leg and prosthetic leg 2 is prepared to be advanced in preparation for the next phase of the gait cycle. Heel 12A is lifted off the ground, thereby causing the stance control valve mechanical or electrical operating arrangement, as the case may be, to allow valve 70 to return to its normally open position. This allows free passage of fluid through unit 7B and allows knee control unit 7B to flex.

During the toe-off stage of the gait cycle, the amputee prepares to advance the limb into the swing phase as the toe leaves the ground, whereupon prosthetic leg 2 is flexed at knee control unit 7B and the hip is flexed to provide the necessary walking surface clearance, thus allowing prosthetic foot 12 to clear surface 13 while it is in the swing phase. At this point, there is obviously no weight on heel 12A and stance control valve 70 is in its normally open position, thereby allowing free passage of fluid 31A and thus allowing flexion of knee control unit 7B. The swing phase as heretofore described occurs when prosthetic leg 2 is advanced in preparation to re-start the gait cycle.

With continued reference to FIG. 3, it will now be understood that valve 70 is placed in the path of flow control valve 76 and is actuated by valve lever 100 attached to stance valve cam 74. The arrangement is such that lever 100 operates valve cam 74 to block or enable fluid flow through valve 70 and flow control valve 76 to affect (compress) bladder 84. Thus, lever 100 can be moved to prevent the flow through flow control valve 74 so as to prevent fluid flow to the bladder which inhibits the displacement of piston 68A to prevent flexion of knee unit 7B.

Lever 100 is controlled mechanically by a choke type cable attached to the lever or electrically via an electronic switch and servo arrangement as will be next described.

Figure 4:
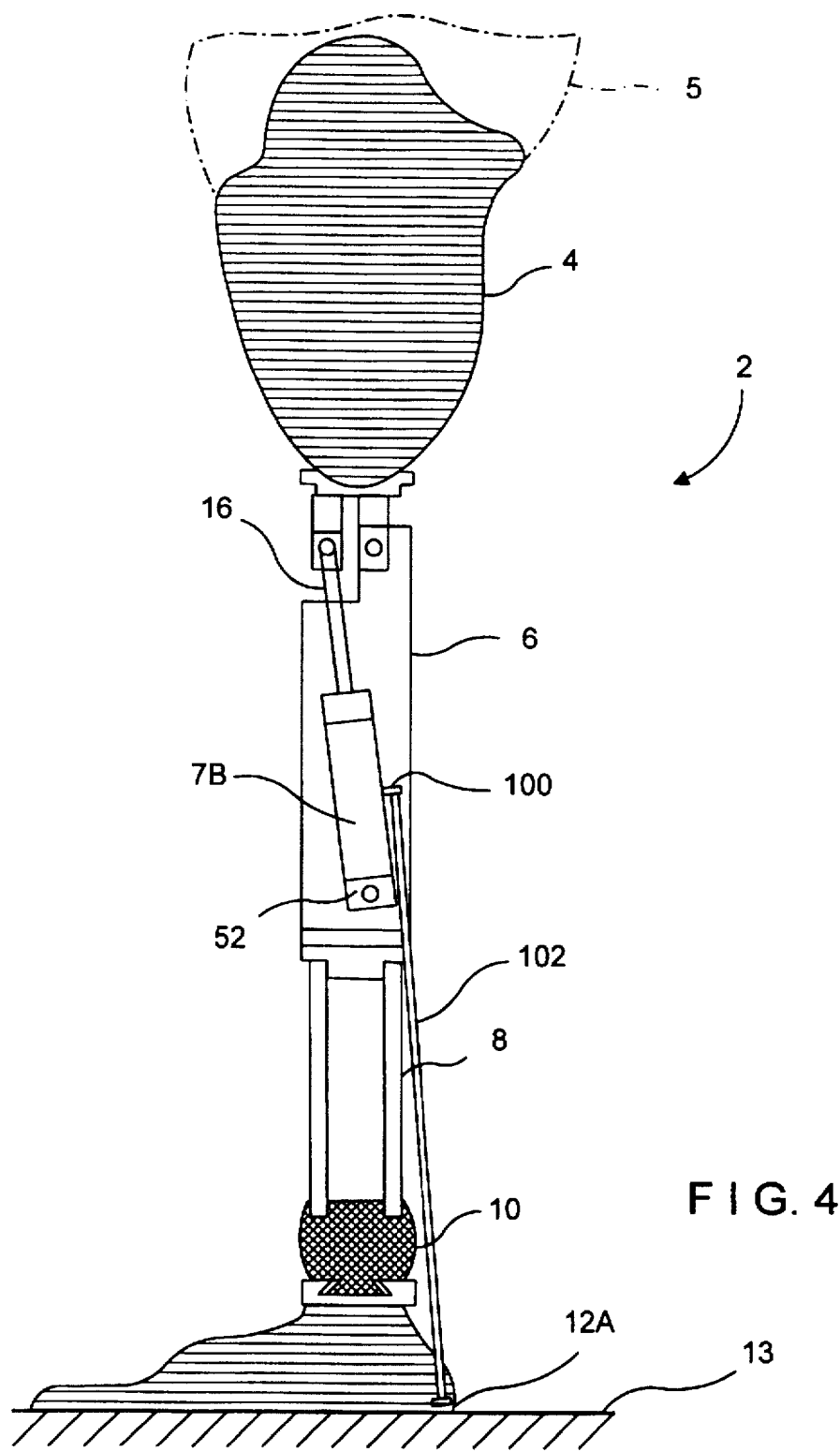
FIG. 4 is a diagrammatic representation illustrating one form of a control arrangement for the control unit shown in FIG. 3.

Thus, with reference first to FIG. 4, a cable 102 is attached to stance valve lever 100 on the proximal end of the cable and is attached to the bottom of heel 12A of prosthetic foot 12 at the distal cable end. When weight is applied to heel 12A at the various stages of gait as aforenoted, the cable pushes on lever 100 so as to actuate stance valve 70 to block fluid flow as described with reference to FIG. 3, whereby knee control unit 7B is prevented from flexing.

Figure 5:
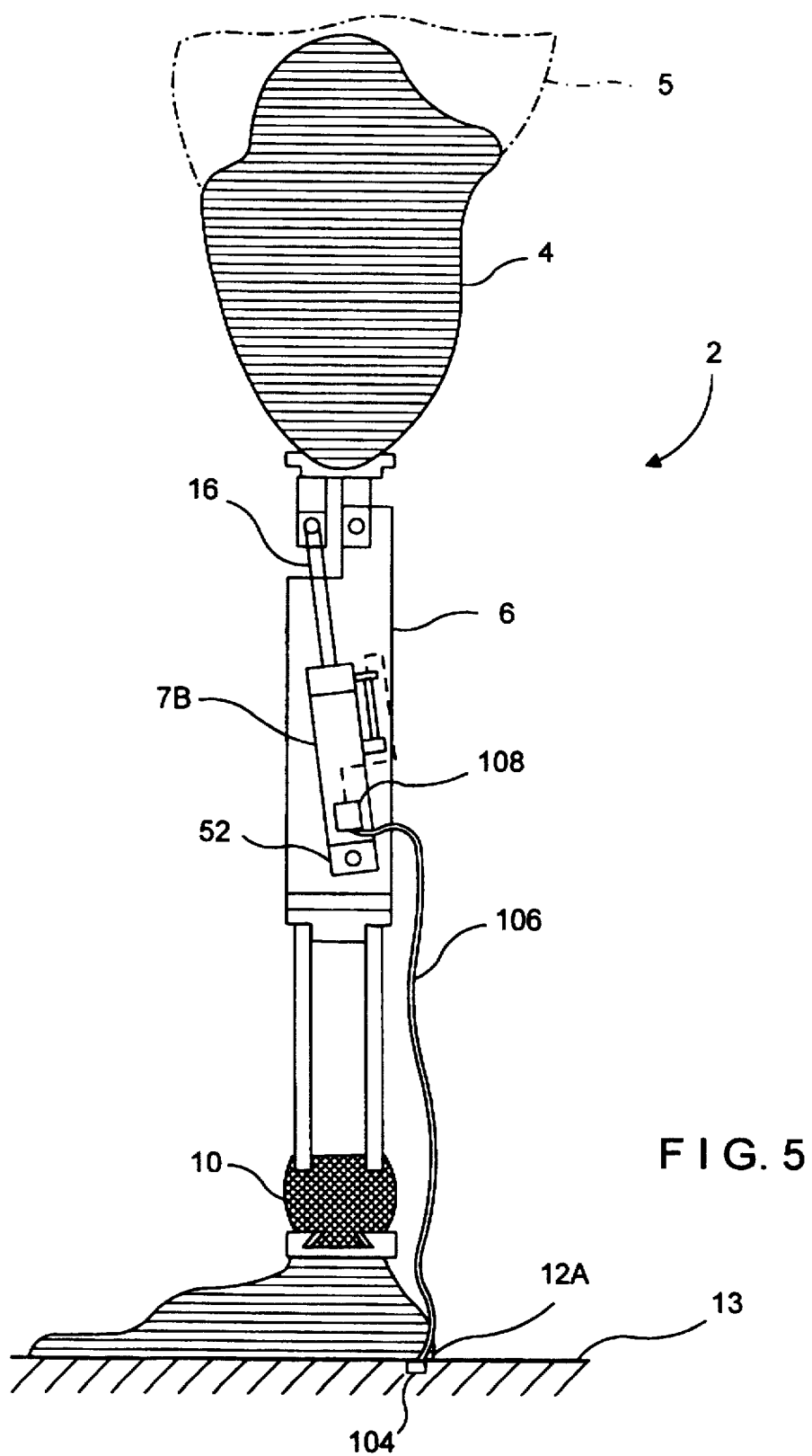
FIG. 5 is a diagrammatic representation illustrating another form of a control arrangement for the control unit shown in FIG. 3.

Alternatively, an electrical arrangement using a switch 104 connected via an electrical connector 106 to a servo mechanism 108 such as illustrated in FIG. 5 may be used for the purposes described. Either of the arrangements shown in FIGS. 4 and 5 are effective for closing valve 70 precisely when knee extension stability is necessary. This provides the stability that is necessary at heel strike and through the mid-stance portion of the gait cycle to insure safe and efficient ambulation of the amputee.

In this regard, it will be understood that valve cam 74 is arranged so that the valve 70 always permits flow when there is no weight on the heel of the prosthetic foot. This enables flexion of the knee during the heel off, toe off and swing phase portion of the gait cycle.

Because of the simplicity of the described arrangement, the size and weight of the knee control units 7A and 7B can be kept to a minimum. Fabrication requires no special equipment or tooling and therefore does not present any unique or unsolvable problems. Costs of producing the control units as described can likewise be kept to a minimum, as is advantageous.

With the above description of the invention in mind, reference is made to the claims appended hereto for a definition of the scope of the invention.

What is claimed is:

1. A prosthetic leg comprising:
   an upper prosthetic limb member;
   a lower prosthetic limb member;
   an operating cylinder, a piston movably disposed within said operating cylinder, said piston separating said operating cylinder into first and second operating chambers;
   said upper prosthetic limb member being connected to said piston;
   a flexible bladder having at least an exterior portion, said bladder situated within a bladder cylinder, said operating cylinder being separated from said bladder cylinder by a solid intermediate region, said second operating chamber being adjacent to said solid intermediate region;
   a valve arrangement situated within said solid intermediate region, said valve arrangement providing communication and controlling a flow of fluid through said solid intermediate region between said bladder cylinder and said second operating chamber of said operating cylinder; and
   said piston being responsive to operation of said prosthetic leg and discharging said fluid in a pressurized form from said second operating chamber via said valve arrangement to said bladder cylinder, while in said bladder cylinder said pressurized fluid acting upon said exterior portion compresses said bladder to store the energy required to drive a prosthetic leg and to provide bias and flexion resistance for the prosthetic leg.

2. The prosthetic leg of claim 1, wherein said bladder cylinder is adjacent to said lower prosthetic limb member and said valve arrangement consists of:
   a valve body disposed within said solid intermediate region;
   a flow control valve disposed within the valve body;
   a check valve disposed within the valve body and arranged for prohibiting passage of the fluid through said flow control valve so as to exteriorly compress the bladder upon flexion of the prosthetic leg during an extension cycle of said prosthetic leg.

3. The prosthetic leg of claim 2, wherein the flow control valve is adjustable to control the flow of the fluid through said flow control valve upon flexion of the knee during the extension cycle of said prosthetic leg.

4. The prosthetic leg of claim 2, wherein the check valve is adjustable to control the flow of the fluid through the flow control valve and thereby control the rate of extension of the prosthetic leg during the extension cycle.

5. The prosthetic leg of claim 4, wherein the check valve is adjustable to provide precise prosthetic leg extension bias control.

6. The prosthetic leg of claim 5, wherein the check valve is adjustable to provide the flow of fluid in addition to that provided by the flow control valve to control the extension cycle of the prosthetic leg.

7. The prosthetic leg of claim 1, further including:
   a bladder valve disposed within the flexible bladder and adjustable for controlling the compressibility of the flexible bladder to provide prosthetic leg bias extension control for controlling the flexion resistance and an extension cycle of the prosthetic leg.

8. A prosthetic leg comprising:
   an upper prosthetic limb member;
   a lower prosthetic limb member;
   an operating cylinder, a piston movably disposed within said operating cylinder, said piston separating said operating cylinder into first and second operating chambers;
   said upper prosthetic limb member being connected to said piston;
   a flexible bladder having at least an exterior portion, said bladder situated within a bladder cylinder, said operating cylinder being separated from said bladder cylinder by a solid intermediate region, said second operating chamber being adjacent to said solid intermediate region;
   a valve arrangement situated within said solid intermediate region, said valve arrangement providing communication and controlling a flow of fluid through said solid intermediate region between said bladder cylinder and said second operating chamber of said operating cylinder; and
   said piston being responsive to operation of said prosthetic leg and discharging said fluid in a pressurized form from said second operating chamber via said valve arrangement to said bladder cylinder, while in said bladder cylinder said pressurized fluid acting upon said exterior portion compresses said bladder to store the energy required to drive a prosthetic leg and to provide bias and flexion resistance for the prosthetic leg; and an actuating device for actuating said valve arrangement, so that said valve arrangement is responsive to weight being applied to a heel of a prosthetic foot at various stages of a gait cycle thereof, whereby the prosthetic leg is permitted to flex or is prevented from flexing via exterior compression of the flexible bladder to provide stability during various stages of the gait cycle for achieving stance control.

9. The prosthetic leg of claim 8, wherein said bladder cylinder is adjacent to said lower prosthetic limb member and said valve arrangement consists of:

a valve body disposed within said solid intermediate region;

a cam actuated valve disposed within the valve body, said cam actuated valve being associated with said actuating device and including a blocking device operable between open and closed positions, so that in said closed position said fluid flow is blocked from and in said open position said fluid is capable of passing through said cam actuated valve;

a check valve disposed within the valve body and arranged for prohibiting passage of the fluid therethrough and permitting passage of said fluid through said cam actuated valve when said blocking device is in the open position.

10. The prosthetic leg of claim 9, further comprising a bladder valve arranged with the bladder and adjustable for varying the compressibility of said bladder.

11. The prosthetic leg of claim 9, further comprising a bleeder valve and a flow control valve adjustable to vary the flow of the fluid therethrough, said flow control valve being disposed in series with said cam actuated valve.

12. The prosthetic leg of claim 11, further comprising a second check valve adjustable to provide a fluid passage in addition to that provided by the flow control valve.

13. The prosthetic leg of claim 11, wherein an actuating arrangement is provided with the cam actuated valve and the prosthetic leg for blocking and enabling fluid flow through the cam actuated valve and is effective for blocking said fluid flow when the heel of the prosthetic foot of a prosthetic leg strikes a walking surface, so that flexing of the prosthetic leg is prohibited.

14. The prosthetic leg of claim 13, wherein the actuating arrangement comprises:

a device for opening and closing the cam actuated valve;

cable means coupled at a proximal end to the opening and closing device and coupled at a distal end to a bottom of the heel of the prosthetic foot; and said cable means being effective for actuating the opening and closing device to close said device to block fluid flow when a force is applied by an amputee to the bottom of the heel of the prosthetic foot, and to open said device to permit fluid flow when said force is relieved.

15. The prosthetic leg of claim 13, wherein the actuating arrangement includes:

a device for opening and closing the cam actuated valve;

a switch supported on a bottom of the heel of the prosthetic foot;

servo arrangement electrically connected to the switch and coupled to the opening and closing device to close the device to block the fluid flow when a force is applied by an amputee to said switch, and to open said device to permit fluid flow when said force is relieved.

16. The prosthetic leg of claim 9, wherein the cam actuated valve is normally open, whereby fluid flows through said cam actuated valve when the prosthetic leg is advanced in a gait cycle and flows around the blocking device and enabling fluid flow through at least said cam actuated valve, whereby the bladder is exteriorly compressed and stores energy for extending the flexed prosthetic leg to continue the gait cycle.

* * * * *